United States Patent
Masuda et al.

(10) Patent No.: US 8,365,576 B2
(45) Date of Patent: Feb. 5, 2013

(54) METHOD FOR DETECTING LOW CONCENTRATION GAS

(75) Inventors: Hideki Masuda, Okazaki (JP);
Tomohiko Inomata, Nagoya (JP); Taku Sawaki, Nagoya (JP)

(73) Assignee: National University Corporation Nagoya Institute of Technology, Nagoya (JP)

( * ) Notice: Subject to any disclaimer, the term of this patent is extended or adjusted under 35 U.S.C. 154(b) by 485 days.

(21) Appl. No.: 12/591,599

(22) Filed: Nov. 24, 2009

(65) Prior Publication Data
US 2010/0294020 A1 Nov. 25, 2010

(30) Foreign Application Priority Data
May 22, 2009 (JP) ................................. 2009-124040

(51) Int. Cl.
*G01N 29/036* (2006.01)
(52) U.S. Cl. ..................................... 73/24.06; 73/24.01
(58) Field of Classification Search ................. 73/24.01, 73/24.06
See application file for complete search history.

(56) References Cited

U.S. PATENT DOCUMENTS
2008/0170986 A1 7/2008 Kitamura et al.

FOREIGN PATENT DOCUMENTS
JP  A-2006-76875  3/2006
JP  A-2009-68974  4/2009

OTHER PUBLICATIONS

Huang, Honghu et al. A Highly Sensitive QCM Sensor Coated with Ag+ZSM-5 Film for Medical Diagnosis. Sensors and Actuators B 101 (2004) 316-321.*
Sawaki et al., "Observation of Absorption Characteristics of Zeolite Encapsulating Metal Complex for Volatile Molecules using Quartz Crystals Microbalance Method," 24th *Meeting for the Presentation of Research on Zeolite*, Japan Association of Zeolite, Nov. 26, 2008, p. 73 (with partial translation).
Jana et al., "Anchoring of Copper Complex in MCM-41 Matrix: A Highly Efficient Catalyst for Epoxidation of Olefins by *tert*-BuOOH," *Langmuir*, 2007, pp. 2492-2496, vol. 23, No. 5.
Pellejero et al., "An Optochemical Humidity Sensor Based on Immobilized Nile Red in Y Zeolite," *Ind. Eng. Chem. Res.*, 2007, pp. 2335-2341, vol. 46, No. 8.
Ray et al., "Encapsulation of Cobalt Phthalocyanine in Zeolite-Y: Evidence for Nonplaner Geomety," *Inorganic Chemistry*, 2003, pp. 1711-1719, vol. 42, No. 5.
Abstract of Yamamoto et al., "Encapsulation of Two Independent Functional Metal Complexes in Nanoporous Material Zeolite and its Catalytic Activity," *J. Porphyrins Phthalacyanines*, 2006, vol. 10, p. 920.
Mintova et al., "Humidity Sensing with Ultrathin LTA-Type Molecular Sieve Films Grown on Piezoelectric Devices", *Chem. Mater.*, 2001, pp. 901-905, vol. 13, No. 3.

*Primary Examiner* — Hezron E Williams
*Assistant Examiner* — Paul West
(74) *Attorney, Agent, or Firm* — Oliff & Berridge, PLC

(57) ABSTRACT

Disclosed is a method for detecting a low concentration gas. In the method, a measurand gas containing the target gas in a concentration of 50 ppm or less is supplied to an oscillation element which contains a quartz crystal resonator and a zeolite including a metal complex (such as a zeolite including a cobalt phthalocyanine complex) present on or above the quartz crystal resonator. The target gas is then detected through a change in resonance frequency of the quartz crystal resonator, the change being caused by the adsorption of the target gas by the metal-complex-including zeolite.

16 Claims, 3 Drawing Sheets

METHOD FOR DETECTING LOW CONCENTRATION GAS

FIELD OF THE INVENTION

The present invention relates to a technique for detecting a target gas (for example, a volatile organic compound) in a low concentration of, for example, 50 ppm or less. More specifically, it relates to a method for detecting such a low concentration gas; a sensor for use in the detection method; and a component of the sensor.

RELATED ART OF THE INVENTION

There are known sensors based on quartz crystal microbalance (QCM) techniques. These sensors utilize the phenomenon that, when a substance is attached to the surface of a quartz crystal resonator, the resonance frequency of the quartz crystal resonator changes in an amount in certain relation with the mass of the attached substance.

Japanese Unexamined Patent Application Publication No. 2009-68974 of the present inventors discloses a quartz crystal resonator having a composition layer, which layer contains a powder of zeolite including a metal complex (hereinafter simply referred to as "quartz crystal resonator having a complex-including-zeolite layer), a method for manufacturing the quartz crystal resonator, and a sensor containing the quartz crystal resonator. Examples of the zeolite including a metal complex can be found typically in Japanese Unexamined Patent Application Publication No. 2006-76875. In the technique disclosed in Japanese Unexamined Patent Application Publication No. 2009-68974, the sensor response is evaluated by supplying air containing 0.1 percent by volume (1000 ppm) of toluene to the quartz crystal resonator having a complex-including-zeolite layer and to another quartz crystal resonator having no complex-including-zeolite layer (blank), and comparing the change in frequency between the two quartz crystal resonators.

However, this patent document fails to compare the sensor response between such a quartz crystal resonator containing a metal-complex-including zeolite and a regular zeolite (i.e., zeolite including no metal complex). It is therefore advantageous to provide a technique for further exerting effects of the use of a quartz crystal resonator supporting or bearing not a regular zeolite but a metal-complex-including zeolite.

SUMMARY OF THE INVENTION

Accordingly, an object of the present invention is to provide a method for detecting a low concentration gas by more effectively using characteristic properties of a metal-complex-including zeolite supported on a quartz crystal resonator. Another object of the present invention is to provide a sensor for use in the detection method, and to provide a component of the sensor.

The present inventors made intensive and detailed investigations on the difference in sensor response between a regular zeolite and a metal-complex-including zeolite, each supported on a quartz crystal resonator. As a result, they have found that the difference in sensor response is not always distinct in the measurand gas (air containing 1000 ppm of toluene) used in the technique disclosed in Japanese Unexamined Patent Application Publication No. 2009-68974. They further found that a quartz crystal resonator supporting a metal-complex-including zeolite behaves in gas adsorption in a distinctive manner quite different from a quartz crystal resonator supporting a regular zeolite under specific gas detection conditions. The present invention has been made based on these findings.

According to an embodiment of the present invention, there is provided a method for detecting a low concentration target gas (typically, a gas of organic compound) contained in a measurand gas. The detection method includes the step of supplying the measurand gas to an oscillation element containing a quartz crystal resonator and a metal-complex-including zeolite present on or above the quartz crystal resonator. The metal-complex-including zeolite may be present typically on an electrode of the resonator. The concentration of the target gas in the measurand gas is 50 ppm or less, and typically 0.1 ppm or more. The target gas is detected through a change in resonance frequency of the quartz crystal resonator, the change caused by adsorption of the target gas contained in the measurand gas by the metal-complex-including zeolite.

In a measurand gas containing the target gas in a relatively high concentration (typically 500 ppm or more, for example, about 1000 ppm), there is no distinct difference in frequency change of a quartz crystal resonator between an oscillation element (QCM sensing element) including a quartz crystal resonator supporting a metal-complex-including zeolite and an oscillation element including a quartz crystal resonator supporting a regular zeolite (i.e., zeolite including no metal complex). However, a measurand gas containing the target gas in a remarkably low concentration (typically 50 ppm or less, further typically 30 ppm or less, and for example, 20 ppm or less), there is significant difference in adsorption behavior of the target gas between the metal-complex-including zeolite and the regular zeolite each supported on the quartz crystal resonator. Specifically, the oscillation element supporting the regular zeolite shows no or substantially no frequency drop, but the oscillation element supporting the metal-complex-including zeolite shows a large frequency drop as a result of adsorption. The gas detection method disclosed herein allows the detection of a low concentration target gas with high sensitivity by effectively utilizing the distinctive gas adsorption behavior of such a metal-complex-including zeolite, which gas adsorption behavior differs from that of, for example, zeolite containing no metal complex. In other words, the encapsulation of a metal complex in zeolite dramatically increases the sensitivity for gas detection.

As used herein the term "metal-complex-including zeolite" refers to a zeolite in which a metal complex is encapsulated or housed in at least part in number of unit cells (pores) constituting the zeolite. In the "metal-complex-including zeolite", the metal complex may partially protrudes out of the unit cell.

According to another embodiment of the present invention, there is further provided a method for using an oscillation element which includes a quartz crystal resonator and a metal-complex-including zeolite present on or above the quartz crystal resonator. The metal-complex-including zeolite may be present typically on an electrode of the resonator. The method includes the steps of supplying a measurand gas containing a target gas in a concentration of 50 ppm or less to the oscillation element; and detecting the target gas through a change in resonance frequency of the quartz crystal resonator caused by the adsorption of the target gas by the metal-complex-including zeolite. This method allows high-sensitivity detection of the low concentration target gas by effectively utilizing the distinctive gas adsorption behavior of the metal-complex-including zeolite. In other words, the oscillation element is advantageously usable as an element for detecting a target gas in a low concentration (typically 50 ppm or less).

In one preferred embodiment of the method disclosed herein, the oscillation element is one including a powder of the metal-complex-including zeolite supported on the quartz crystal resonator without using a binder. The powder of metal-complex-including zeolite may be supported typically on an electrode of the resonator. To allow a predetermined member to support a powdery material, a binder is generally used for binding particles constituting the powdery material with each other or binding the particles with the surface of the member. The binder may be an organic substance, such as a thermoplastic polymer, and/or an inorganic substance such as fine ceramic particles. The use of such a binder, however, can increase the noise in the vibration (typically, thickness-shear vibration) of a quartz crystal resonator. In addition, the binder (especially an organic binder), if attached to the powder of metal-complex-including zeolite, may cause the powder to vary in its surface area, and this may vary the gas adsorption behavior. These events can cause the detection sensitivity to decrease or cause the detection error to increase. An oscillation element used in the detection of a low concentration gas as disclosed herein preferably employs at least no organic binder and especially preferably employs neither organic binder nor inorganic binder. The oscillation element having the configuration can detect a low concentration target gas more precisely.

An exemplary process for allowing a quartz crystal resonator to support a powder of metal-complex-including zeolite without using a binder includes a process of preparing a suspension in which the binder is highly dispersed in a suitable solvent, applying the suspension to a surface of the quartz crystal resonator, and air-drying the applied suspension. The solvent herein may for example be a solvent mixture of water and a low-boiling organic solvent. A preferred process for preparing the suspension will be mentioned later.

The metal-complex-including zeolite is preferably a zeolite including a metal phthalocyanine complex (for example, cobalt phthalocyanine complex) encapsulated in one or more zeolite unit cells. The metal phthalocyanine complex, if not encapsulated in the unit cells, has a substantially planar shape, and thereby two or more complex molecules are liable to stack on each other. The stacking of complex molecules can be avoided by encapsulating the metal phthalocyanine complex in zeolite unit cells. This helps the metal-complex-including zeolite to adsorb the target gas more effectively. The encapsulation is typically performed so that each one complex molecule is encapsulated in one unit cell, respectively. Such metal phthalocyanine complexes are preferred also because they show superior affinity for some typical target gases such as toluene, pyridine, and acetaldehyde. Metal salophen complexes are also listed as other examples of metal complexes which are liable to stack outside of zeolite unit cells and which are encapsulated in unit cells with great significance.

Exemplary preferred zeolites for the technique disclosed herein include zeolite X and zeolite Y. For example, zeolite X including a cobalt phthalocyanine complex encapsulated in its unit cells is preferably employed.

According to yet another embodiment of the present invention, there is provided a gas sensor for the detection of a target gas contained in a low concentration (typically 50 ppm or less, further typically 30 ppm or less, and for example 20 ppm or less) in a measurand gas. The gas sensor includes an oscillation element which has a quartz crystal resonator and a metal-complex-including zeolite present on or above the quartz crystal resonator. The sensor may further include a measurand gas supply unit for supplying the measurand gas to the oscillation element. The measurand gas supply unit can also be grasped as a measurand gas supply means. Independently, the sensor may further include a frequency counter for measuring the resonance frequency of the quartz crystal resonator. The frequency counter can also be grasped as a frequency measuring means.

The gas sensor having the configuration is suitable as a sensor to perform any of the detection methods of a low concentration gas disclosed herein. In other words, any of the detection methods of a low concentration gas disclosed herein is preferably performed by using the gas sensor having the configuration.

According to still another embodiment of the present invention, there is provided a method for manufacturing an oscillation element which includes a quartz crystal resonator and a metal-complex-including zeolite present on or above the quartz crystal resonator. The metal-complex-including zeolite may be present typically on an electrode of the resonator. The manufacturing method includes the step of preparing a powder of a zeolite including a metal complex encapsulated in a zeolite unit cell. The metal complex may typically have a size larger than that of an opening of the unit cell. The method may further include the step of placing the powder of metal-complex-including zeolite in a solvent and homogenizing the powder in the solvent through ultrasonic disintegration to give a suspension, and may further include the step of applying the suspension prepared through homogenization to a surface of an electrode of a quartz crystal resonator and drying the applied suspension. The drying may be performed typically through air drying. The suspension to be applied to the surface of the electrode preferably contains substantially no binder. As used herein the term "containing substantially no binder" refers to that an organic binder and/or inorganic binder is not incorporated into the suspension at least intentionally. It is desirable, for example, to apply a suspension containing, as nonvolatile contents, the powder of metal-complex-including zeolite alone to the surface of the electrode.

The oscillation element manufactured by the method is suitable as an oscillation element for use in any of the gas detection methods disclosed herein. This oscillation element is also suitable as a component for any of the gas sensors (typically, the gas sensor designed specifically for a gas in a low concentration of 50 ppm or less) disclosed herein.

BRIEF DESCRIPTION OF THE DRAWINGS

Other objects, features and advantages of the present invention will be understood more fully from the following detailed description made with reference to the accompanying drawings. In the drawings.

DETAILED DESCRIPTION OF THE PREFERRED EMBODIMENTS

Figure 1:
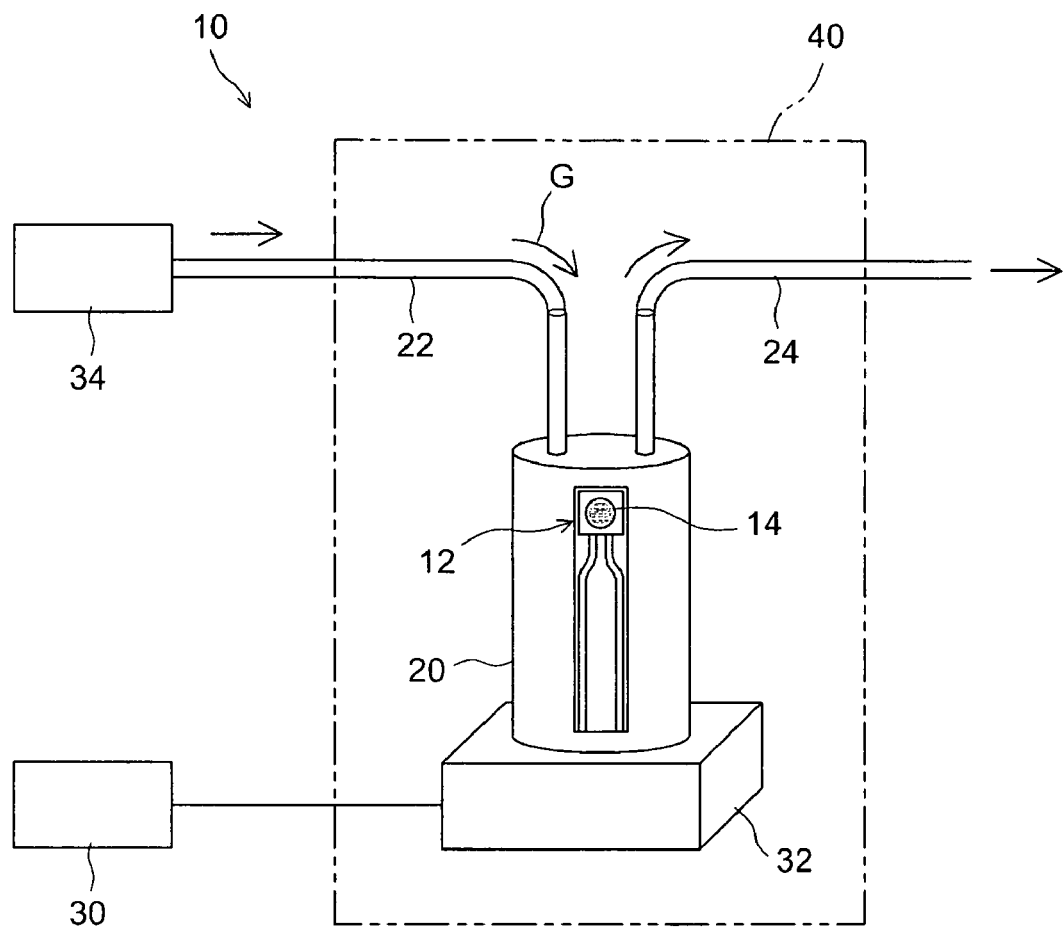
FIG. 1 is a schematic view illustrating a schematic structure of a gas sensor according to one embodiment of the present invention.

The present invention will be described further with reference to various embodiments in the drawings.

The present invention will be illustrated in detail with reference to some preferred embodiments below. Matters necessary for carrying out the present invention, except those specifically referred to in the present specification, can be grasped as design matters of those skilled in the art based on known technologies in the art. The present invention can be carried out based on the contents disclosed herein and technical common sense in the art.

A metal-complex-including zeolite in the technique disclosed herein contains a zeolite and a metal complex encapsulated or housed in a unit cell of the zeolite. Zeolites for constituting the metal-complex-including zeolite are not limited to known porous crystalline aluminosilicates but can also be inorganic materials having similar crystal structures (skeleton structures), such as porous crystalline metallosilicates and porous crystals of phosphates. These inorganic materials having crystal structures similar to those of porous crystalline aluminosilicates (hereinafter also referred to as "zeolite-type crystal structure(s)") are described in detail in the book released in July of 2000 entitled, "The Science and Industry of Zeolite," (Yoshio ONO and Tateaki YASHIMA, published by Kodansha). As used herein the term "zeolite" can conceptually include various inorganic materials having zeolite-type crystal structures. Also as used herein the term a "unit cell" of zeolite refers to a structural unit in the crystal structure (skeleton structure) of the zeolite. The "unit cell" also acts as a unit to constitute one pore in the zeolite.

Examples of specific structure of the zeolite include large-pore zeolites, in which the structural pore openings each include twelve atoms, such as zeolite X, zeolite Y, gmelinite, zeolite β, mordenite, of fretite, EMT, SAPO-37, and beryllophosphate X; extra-large-pore zeolites in which the structural pore openings each include fourteen or more atoms, such as cloverite; medium-pore zeolites in which the structural pore openings each include ten atoms, such as ferrierite, heulandite, and weinebeneite; and small-pore zeolites in which the structural pore openings each include eight or fewer atoms, such as analcime, chabazite, erionite, and zeolite A. Of these, zeolites X and Y, EMT, SAPO-37, and beryllophosphate X have preferred structures for including a single molecule of metal complex per unit cell to constitute a metal-complex-including zeolite because they have an internal pore diameter of 1.3 nm and a pore opening diameter of 0.7 nm. Among them, zeolite X and/or zeolite Y is especially preferred.

In general, zeolites include cations that neutralize the charge of the skeleton structure (typically, a skeleton structure including silicon and aluminum coupled with each other through oxygen). The cations can be any of cations of one or more members selected from, for example, alkali metals such as lithium, sodium, and potassium; and alkaline earth metals such as magnesium, calcium, and barium. The cations herein can also be cations of one or more metals selected from metals belonging to Groups 4 to 13 of the periodic table, such as silver, copper, zinc, platinum, palladium, aluminum, indium, tin, titanium, vanadium, chromium, manganese, iron, cobalt, nickel, ruthenium, osmium, rhodium, iridium, gold, molybdenum, and tungsten; and rare-earth metals (including lanthanoid elements) such as lanthanum and cerium. Part or substantial all of these cations can be exchanged by other cations (secondary ions) typically through ion exchange.

The metal complex to be encapsulated in the zeolite can be any of various metal complexes as selected depending on the type of a target gas so as to have affinity for the target gas at least when encapsulated in the zeolite. For example, metal phthalocyanine complexes are listed as exemplary metal complexes suitable for the detection of representative volatile organic compounds (VOCs), toluene, pyridine, and acetaldehyde. The metal complex to be encapsulated in the zeolite may be a metal complex that does not adsorb the target gas when existing alone (not encapsulated in the zeolite). Typically, when the target gas is toluene, pyridine, or acetaldehyde, a cobalt phthalocyanine complex does not adsorb the target gas when existing alone, but can adsorb the target gas when encapsulated in a zeolite X unit cell.

As used herein the term "metal phthalocyanine complex" conceptually includes not only one whose ligand constituting the metal complex has no substituent (i.e., is unsubstituted) but also one whose ligand has one or more substituents. The same is true for other complexes. One preferred example of the metal-complex-including zeolite as disclosed herein is a zeolite including an unsubstituted metal phthalocyanine complex represented by following Formula (A), wherein "M" represents a central metal. Such a metal phthalocyanine complex is preferred because it can be easily synthesized within a zeolite unit cell according to a ship-in-bottle process using relatively inexpensive raw materials.

(Chemical formula 1)

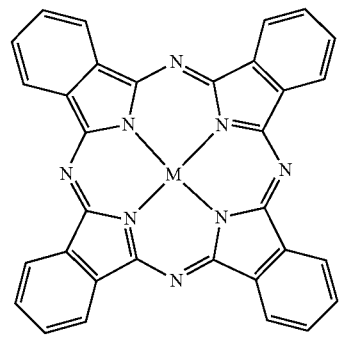

(A)

Other examples of metal complexes preferably employed in the technique disclosed herein include bis(salicylidene)-o-phenylenediaminato metal complexes (hereinafter also referred to as "metal salophen complexes"); metal complexes containing a cyclic tetrapyrrole compound, such as porphyrin or porphycene, as a ligand; and metal complexes containing a polypyridyl compound, such as pyridine or terpyridine, as a ligand.

The central metal consisting the metal complex can be, for example, cobalt (Co), iron (Fe), manganese (Mn), copper (Cu), nickel (Ni), titanium (Ti), ruthenium (Ru), zinc (Zn), chromium (Cr), platinum (Pt), palladium (Pd), vanadium (V), and cerium (Ce). Of these, preferred as central metals are cobalt, iron, manganese, copper, nickel, titanium, and ruthenium, because complexes containing these metals are easily synthetically available, they are especially suitably synthetically available according to the ship-in-bottle process, their capabilities of adsorbing the representative VOCs are high when encapsulated in the zeolite, and their raw materials are inexpensively available.

In one preferred embodiment, a metal-complex-including zeolite including a metal complex having a size larger than the size of the pore opening of unit cell constituting the zeolite is used. The size of pore opening of, for example, zeolites X and Y is about 0.7 nm. In other words, the zeolite preferably includes a metal complex having such a size as not to pass through the opening substantially (i.e., such a size that the metal complex does not come in and out from a unit cell pore through the opening). The combination of a zeolite and a metal complex satisfying the condition in size is suitable for stably maintaining the metal complex encapsulated within the unit cell (in the pore). An event where such a metal complex encapsulated in a unit cell escapes out from the pore of the unit cell (i.e., the unit cell loses the metal complex) is liable to occur during various treatments that can be performed on the metal-complex-including zeolite and/or in various uses of the zeolite material. The combination of a zeolite and a metal complex satisfying the condition in size can avoid this event, and its composition is resistant to deterioration even after a treatment such as homogenization through ultrasonic disintegration, and is thereby suitable for the preparation of a suspension containing the powder of metal-complex-including zeolite highly dispersed in a solvent. The powder of metal-complex-including zeolite is therefore suitable for the preparation of an oscillation element which contains the powder supported on a quartz crystal resonator using substantially no binder.

By way of example, the metal complex can be encapsulated in a zeolite unit cell by heating a mixture of the zeolite and a raw material for the formation of metal complex (e.g., a precursor of a ligand constituting the complex) in a sealed tube, or by heating the mixture under reflux. The mixture is preferably a mixture containing a zeolite supporting a metal element to be the central metal of the target metal complex to be encapsulated in the unit cell; and a ligand precursor that can coordinate with the metal element to constitute the metal complex. The ligand precursor is preferably a compound having a size smaller than that of the unit cell opening. The encapsulation of the metal complex in the unit cell is preferably performed so that such a ligand precursor coordinates with the metal element within the unit cell to synthesis (constitute) the metal complex within the unit cell. When a metal complex having a size larger than that of the unit cell opening is to be encapsulated in the unit cell, it is preferred to chose the complex and a corresponding ligand precursor (preferably together with a metal element to be the central metal of the complex) so that two or more ligand precursor molecules form one complex molecule. The two or more ligand precursor molecules may be of a compound of one type or compounds of two or more types. Techniques for synthesizing a metal complex within a unit cell (among them, the technique for synthesizing a complex having a size larger than that of the opening of the unit cell) can be grasped as so-called ship-in-bottle processes. According to the synthesis techniques, even a metal complex having a size larger than that of the opening of a unit cell can be efficiently encapsulated in the unit cell. The synthesis techniques are advantageously applicable also to the synthesis of a metal complex having a size smaller than that of the unit cell opening.

The quartz crystal resonator for use in the technique disclosed herein can be any of quartz crystal resonators for use in regular QCM techniques. An AT-cut quartz crystal resonator is generally preferably used. An exemplary preferred quartz crystal resonator has a fundamental resonance frequency $F_0$ of about 9 MHz or more (typically from about 9 MHz to about 30 MHz) and an electrode area A of from about 0.1 $cm^2$ to about 0.5 $cm^2$.

The quartz crystal resonator can be allowed to support a metal-complex-including zeolite to form an oscillation element, for example, in the following manner. The metal-complex-including zeolite herein is typically powdery such as a powder of the metal-complex-including zeolite having an average particle diameter of from 0.1 µm to 0.5 µm. Specifically, a suspension containing a powder of metal-complex-including zeolite dispersed in a suitable solvent is prepared. In addition to the solvent (volatile component) and the metal-complex-including zeolite, the suspension may further contain an organic binder and/or inorganic binder or may contain substantially no binder. The suspension is applied onto a surface of an electrode of the quartz crystal resonator through, for example, dropwise addition, and the solvent is removed (evaporated) therefrom to give an oscillation element which includes the quartz crystal resonator and, supported thereon, the metal-complex-including zeolite. The removal of the solvent may be performed through air drying, or through heating so as to accelerate drying.

In one preferred embodiment, a suspension containing substantially no binder is applied to the quartz crystal resonator. This embodiment can give an oscillation element that can constitute a gas sensor with especially high precision. It is advantageous to disperse the powder of metal-complex-including zeolite to a high degree in the suspension in order to allow the quartz crystal resonator to support the powder of metal-complex-including zeolite without using any binder. The high-degree dispersion is preferably performed by a process including placing a powder of metal-complex-including zeolite in a solvent and subjecting the powder in the solvent to ultrasonic disintegration treatment to thereby homogenize the system (to finely divide the powder). The ultrasonic disintegration treatment can be performed by using a commercially available ultrasonic generator such as the ultrasonic generator supplied under the trade name "TOMYUD-201" by Tomy Seiko Co., Ltd. A treatment for applying ultrasonic vibration to the system (ultrasonic treatment) may be performed in addition to the ultrasonic disintegration treatment. The ultrasonic treatment allows the powder of metal-complex-including zeolite to be dispersed (suspended) further uniformly in the solvent. The ultrasonic treatment can be performed using, for example, a common ultrasonic cleaner. The ultrasonic treatment may be performed simultaneously with, prior to, or subsequent to the ultrasonic disintegration treatment, or at two or more of these periods.

More specifically, the metal-complex-including zeolite can be supported by the quartz crystal resonator preferably in the following manner. Specifically, a powder of metal-complex-including zeolite having an average particle diameter of from 0.1 µm to 0.5 µm is prepared typically through synthesis or purchase. The powder of metal-complex-including zeolite in an amount of 50 mg to 200 mg is placed in 100 mL of water, dispersed therein by applying ultrasonic vibration (ultrasonic treatment), and further homogenized by using an ultrasonic generator (ultrasonic disintegration treatment). The water for use herein is preferably ultrapure water or ion-exchanged water. The ultrasonic disintegration treatment can be performed so as to allow the powder of metal-complex-including zeolite to have an average particle diameter smaller than that before the treatment, in other words, so as to divide the powder particles more finely.

The prepared aqueous suspension of the powder of metal-complex-including zeolite is combined with and mixed with a volatile organic solvent that is uniformly miscible with water. Preferably, the ultrasonic treatment is performed after the addition of the volatile organic solvent. Exemplary volatile organic solvents usable herein include tetrahydrofuran (THF), acetone, and methanol, of which THF, for example, is preferably usable. The volume ratio of water to the volatile organic solvent is generally suitably from about 1:0.2 to about 1:5 and is, for example, from about 1:0.5 to about 1:2. A suspension containing a powder of metal-complex-including zeolite dispersed in the solvent mixture of water and the volatile organic solvent is prepared in this way. It is recommended to apply the resulting suspension to a quartz crystal resonator and drying the applied suspension through air-drying.

The technique disclosed herein may be adopted to constitute a gas sensor. An embodiment of the gas sensor is schematically illustrated in FIG. 1. The gas sensor 10 includes an oscillation element 12; a cell (gas detection unit) 20 that houses the oscillation element 12; and a frequency counter 30 that is electrically connected to the oscillation element 12 and determines the frequency of a quartz crystal resonator 14. The oscillation element 12 includes the quartz crystal resonator 14 and, supported thereon, a metal-complex-including zeolite. The reference numeral 32 stands for an oscillator. Two tubes 22 and 24 are led out from the top end of the cell 20. Of the two tubes, one tube 22 is used as a measurand gas inlet tube to guide a measurand gas G from a measurand gas supply unit 34 to the cell 20, which measurand gas G contains a target gas in a concentration of 50 ppm or less. The other tube 24 is used as an exhaust tube. The cell 20 is arranged within a thermostat 40 so as to maintain the temperature of the cell 20 at a constant level. The cell 20 is preferably maintained at a predetermined constant temperature (such as a temperature selected within the range of from 20° C. to 80° C.) during gas detection. As the target gas contained in the measurand gas G is adsorbed by the metal-complex-including zeolite of the oscillation element 12, the quartz crystal resonator 14 shows a frequency drop. The change in frequency $\Delta F$ is grasped through the frequency counter 30 so as to detect the presence of the target gas.

The gas sensor disclosed herein can further include additional arbitrary components such as an arithmetical unit and a display unit. The arithmetical unit has the function of calculating a concrete increase in mass by substituting the measurement obtained by the frequency counter 30 and necessary parameters into the Sauerbrey equation generally employed in the QCM technologies. The display unit has the function of indicating the detection of the target gas.

The technique disclosed herein is preferably adopted to the detection of a gas in a low concentration of 50 ppm or less (preferably 30 ppm or less, and, for example, 20 ppm or less). The lower limit of detectable concentration is typically 0.1 ppm or more, and for example, 0.5 ppm or more, although the lower limit may vary depending typically on the combination between the target gas and the metal complex, and the dimensions of the quartz crystal resonator. The technique disclosed herein is especially advantageous as a technique for the detection of a low concentration organic compound gas. The technique is preferably adopted to the detection of volatile organic compounds such as toluene, pyridine, acetaldehyde, benzene, and xylenes.

The present invention will be illustrated in further detail with reference to several working examples below. It should be noted, however, that these examples are never intended to limit the scope of the present invention. All "parts" and "percentages" below are by mass, unless otherwise specified.

Preparation of Zeolite Including Cobalt Phthalocyanine Complex

A zeolite X powder including $Co^{2+}$-phthalocyanine complex (CoPc) was prepared according to the following procedure. Specifically, a powder (product supplied by Tosoh Corporation) of zeolite X containing sodium ions (NaX) was prepared, and part of sodium ions ($Na^+$) contained in the zeolite were exchanged with cobalt ions ($Co^{2+}$) through ion exchange to yield NaX containing 0.95 percent by weight of $Co^{2+}$ ions (Co—NaX). In acetone were stirred 108.96 g of the Co—NaX (containing 18 mmol of $Co^{2+}$) and 0.127 mol of o-phthalonitrile for one hour, a volatile component was removed from the react ion mixture, and the residue was suspended in 250 mL of ethylene glycol. The suspension was combined with 15 mL of tri-n-butylamine ($(n-Bu)_3N$), and the mixture was stirred at 210° C. for 5 hours to give a solid. The solid was purified through extraction sequentially with methanol, acetone, and pyridine in a Soxhlet extractor to remove unnecessary substances such as unreacted ligand contained in the solid and phthalocyanine that had formed outside the zeolite pores. The purified product was suspended in 400 mL of a saturated aqueous solution of sodium nitrate, followed by stirring for 24 hours, to remove unreacted cobalt ions that had remained without forming the complex through exchange with sodium ions. The resulting substance was washed with water, dried at 60° C., and thereby yielded a pale blue powder. The energy dispersive X-ray spectroscopy (EDX), ultraviolet-visible (UV/vis) absorption spectra, and diffuse reflection spectra of the powder verified that a target substance (CoPc@NaX) composed of NaX and cobalt phthalocyanine encapsulated in the NaX unit cell was obtained.

Pretreatment of QCM Chip

A QCM chip (AT-cut, 10 MHz, electrode area: 0.159 $cm^2$) was prepared, and an electrode unit thereof was immersed in a concentrated nitric acid for several hours, followed by ultrasonic cleaning with water. Next, a gold electrode was immersed in a piranha solution ($H_2SO_4$:$H_2O$=7:3) for 30 minutes. Thereafter, the QCM chip was retrieved, washed with water, and immediately subjected to an experiment.

Preparation of CoPc@NaX-Supporting QCM Chip

An oscillation element structurally having a QCM chip and CoPc@NaX supported on the QCM chip (CoPc@NaX/QCM) was prepared. Specifically, 100 mg of CoPc@NaX was placed in 100 mL of ultrapure water (Milli-Q water), and this was subjected to an ultrasonic treatment for 2 hours in the ultrasonic cleaner supplied under the trade name "EYELA MUS=20D" (38 kHz, 250 W) by Tokyo Rikakikai Co., Ltd. and thereafter further subjected to a homogenization treatment for 30 minutes using the ultrasonic generator supplied under the trade name "TOMY UD-201" (20 kHz, 200 W) by Tomy Seiko Co., Ltd. A suspension A-1 containing 1 mg/mL of CoPc@NaX dispersed in water was prepared in this manner; To 1 mL of the suspension was added 1 mL of tetrahydrofuran (THF), and the mixture was subjected to an ultrasonic treatment for 10 minutes in the ultrasonic cleaner. A suspension A-2 containing CoPc@NaX dispersed in a 1:1 (by volume) solvent mixture of $H_2O$ and THF was prepared in this manner.

The suspension A-2 (20 μL) was added dropwise onto the pretreated electrode surface of the QCM chip, and was air-dried. This procedure was performed once, or was repeated two more times, and thereby yielded two oscillation element samples (E-1 and E-2) each containing a QCM chip and 40.28 μg of CoPc@NaX supported on the electrode of the QCM chip; and one oscillation element sample (E-3) containing a QCM chip and 13.33 μg of CoPc@NaX supported on the electrode of the QCM chip. The suspension A-2 contains the solvent mixture and CoPc@NaX alone but contains no binder. In other words, CoPc@NaX was supported by QCM without using any binder in these oscillation element samples. There was a good linearity between the amount of the added suspension A-2 and the amount of the supported CoPc@NaX.

The UV/vis absorption spectrum (in $H_2SO_4$) and diffuse reflection spectrum of CoPc@NaX were compared between before and after the ultrasonic treatment and homogenization treatment to find that there was no significant difference between before and after the treatments in all the spectra. The results support that the structure of CoPc encapsulated in NaX is adequately maintained even after the ultrasonic treatment and homogenization treatment.

Preparation of NaX-Supporting QCM Chip

An oscillation element structurally having QCM and NaX supported on the QCM (NaX/QCM) was prepared as a control. The NaX/QCM was prepared by the same procedure as in the preparation of CoPc@NaX/QCM, except for using NaX instead of CoPc@NaX. Specifically, a suspension B-2 containing NaX dispersed in a 1:1 (by volume) solvent mixture of $H_2O$ and THF was initially prepared. The procedure of adding the suspension B-2 dropwise onto the electrode surface of the QCM chip and air-drying the applied suspension was performed once, or repeated two or more times, and thereby yielded two oscillation element samples (F-1 and F-2) each containing a QCM chip and 23.14 μg of NaX supported on the electrode of the QCM chip; and one oscillation element sample (F-3) containing a QCM chip and 10.64 μg of NaX supported on the electrode of the QCM chip.

Gas Detection Test

Tests for detecting a target gas contained in a low concentration of 50 ppm or less (from 1 ppm to 20 ppm, specifically from 2 ppm to 12 ppm herein) in a measurand gas were performed using gas sensors having CoPc@NaX/QCM as an oscillation element, and gas sensors having NaX/QCM as an oscillation element. In these tests, a gas sensor 10 having the schematic configuration illustrated in FIG. 1 was used. The gas sensor 10 includes a cell 20 that houses any of the above-prepared oscillation element 12; and a frequency counter 30 that is electrically connected to the oscillation element 12 and determines the frequency of a quartz crystal resonator 14. The cell 20 herein was one made of glass, and the frequency counter 30 herein was the Universal Counter Model 5313A supplied by Agilent, having a resolution of 0.1 Hz. Two tubes 22 and 24 are led out from the top end of the cell 20. Of the two tubes, one tube 22 is used as a measurand gas inlet tube. In this experimental example, a gas generator 34 (the permeator supplied under the trade name "GASTEC PD-1B-2" by Gastec Corporation) is connected to the measurand gas inlet tube 22 for the evaluation of the response of the oscillation element 12 to the gas composition. The gas generator 34 discharges a measurand gas G prepared as having a predetermined composition. The other tube 24 is used as an exhaust tube. The cell 20 is placed within a thermostat 40. The thermostat 40 herein was the Model LS-5 supplied by Nippon Blower Co., Ltd.

The oscillation element 12 was dried at 100° C. in vacuo immediately before the initiation of measurement to remove the influence of moisture that had been adsorbed by the oscillation element 12. The inside of the thermostat 40 was maintained at 60° C., and the measurand gas G at 40° C. was supplied from the gas generator 34 to the cell 20 at a predetermined flow rate. As the measurand gas, three types of gases were prepared; i.e., a gas (G-1) containing toluene as a target gas in a concentration of 11 ppm in dry air (carrier gas); a gas (G-2) containing pyridine as a target gas in a concentration of 12 ppm in dry air; and a gas (G-3) containing acetaldehyde as a target gas in a concentration of 2 ppm in dry air. Detection tests from the measurand gas G-1 were performed using the oscillation element samples E-1 and F-1 at a flow rate of the measurand gas G-1 of 0.5 liter per minute. Detection tests from the measurand gas G-2 were performed using the oscillation element samples E-2 and F-2 at a flow rate of the measurand gas G-2 of 0.5 liter per minute. Detection tests from the measurand gas G-3 were performed using the oscillation element samples E-3 and F-3 at a flow rate of the measurand gas G-3 of 0.8 liter per minute. Each measurand gas was supplied to a gas sensor including each oscillation element sample for one hour, and the change in frequency during the supply was recorded. The results are shown in FIGS. 2 to 4, in which the ordinate indicates an amount of change in frequency relative to the frequency (zero point) at the beginning of measurement of each oscillation element.

Figure 2:
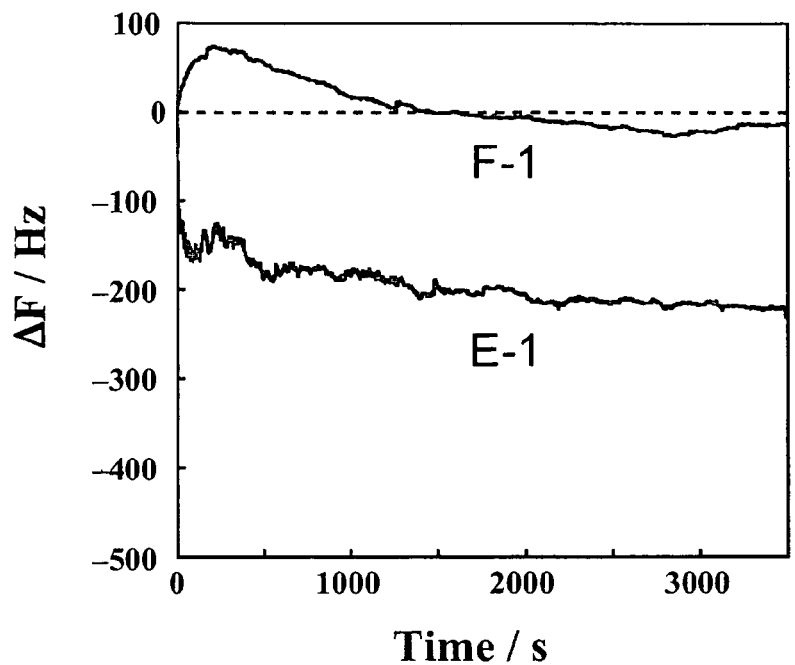
FIG. 2 is a chart showing the change in frequency of an oscillation element E-1 including a quartz crystal resonator and a metal-complex-including zeolite supported on the resonator, and of an oscillation element F-1 including a quartz crystal resonator and, supported thereon, zeolite including no metal complex, as determined when a measurand gas G-1 containing 11 ppm of toluene is supplied to each of the oscillation elements.
Figure 3:
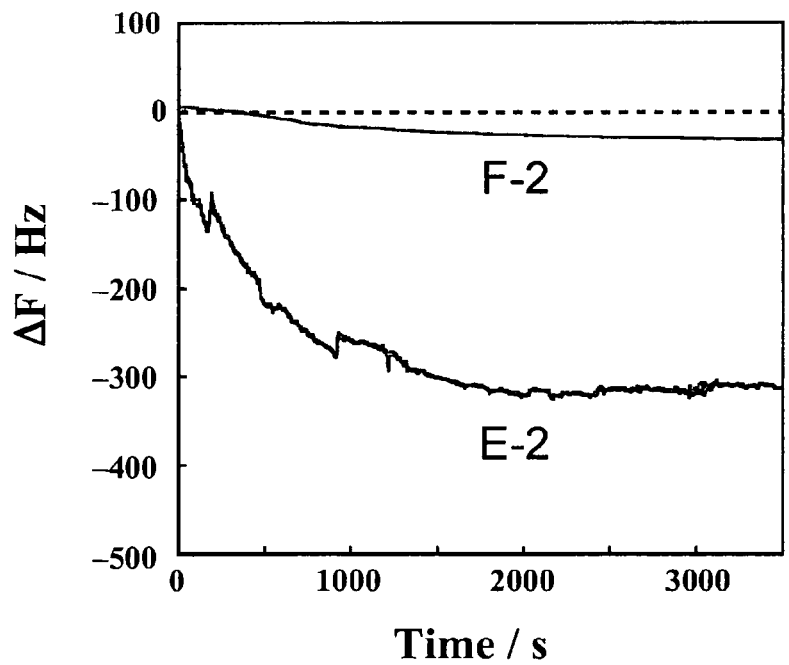
FIG. 3 is a chart showing the change in frequency of an oscillation element E-2 including a quartz crystal resonator and a metal-complex-including zeolite supported on the resonator, and of an oscillation element F-2 including a quartz crystal resonator and, supported thereon, zeolite including no metal complex, as determined when a measurand gas G-2 containing 12 ppm of pyridine is supplied to each of the oscillation elements.
Figure 4:
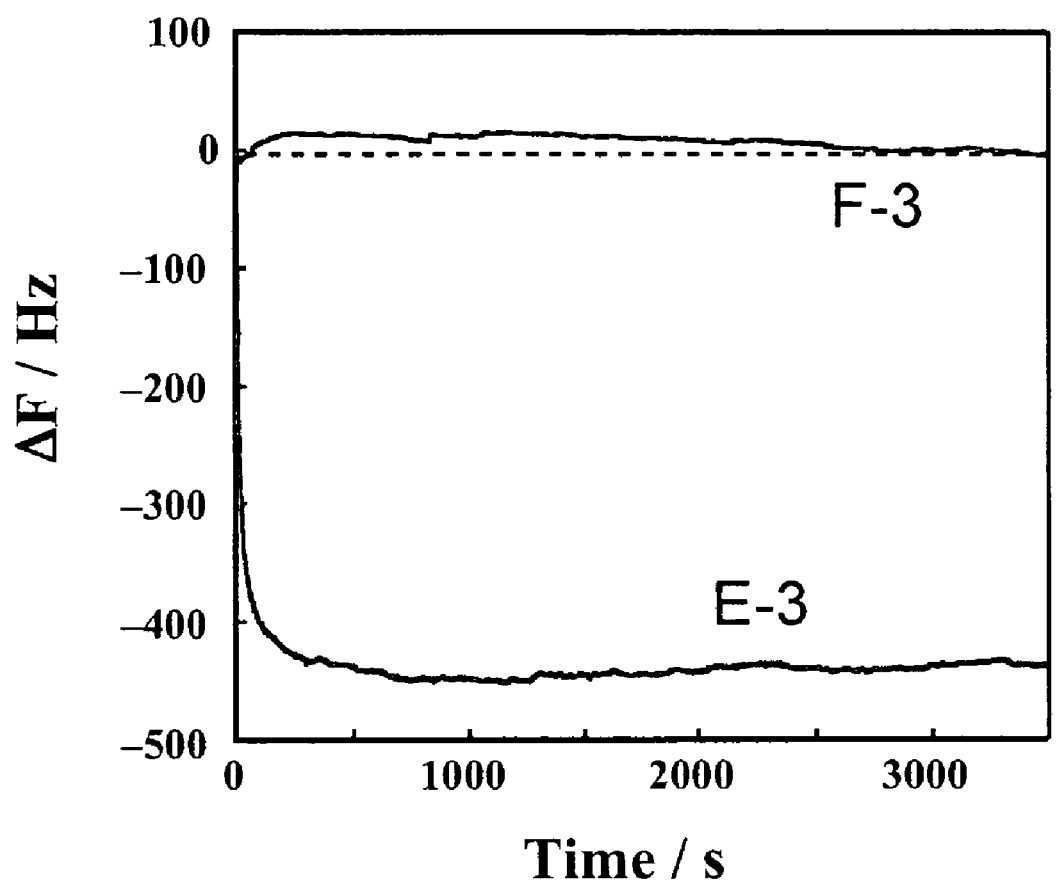
FIG. 4 is a chart showing the change in frequency of an oscillation element E-3 including a quartz crystal resonator and a metal-complex-including zeolite supported on the resonator, and of an oscillation element F-3 including a quartz crystal resonator and, supported thereon, zeolite including no metal complex, as determined when a measurand gas G-3 containing 2 ppm of acetaldehyde is supplied to each of the oscillation elements.

FIGS. 2 to 4 demonstrate that each of the oscillation element samples E-1 to E-3 using CoPc@NaX/QCM showed a large frequency drop (100 Hz or more) within 2 minutes from the beginning of the supply of measurand gas. The frequency change therefore helps to grasp the presence of the target gas in the measurand gas easily and reliably. Specifically, these oscillation element samples E-1 to E-3 were verified to show response performance sufficiently practical as gas sensors for the detection of gases in low concentrations (50 ppm or less).

In contrast, the oscillation element samples F-1 to F-3 using NaX/QCM showed little frequency drop during from the beginning of the measurand gas supply until one hour later. The results demonstrate that zeolite including no metal complex little absorbs the target gases in low concentrations (2 to 12 ppm) as used herein.

Further tests using a measurand gas containing the target gases in higher concentrations (1000 ppm, 10000 ppm) were performed, and the results demonstrate that even zeolite including no metal complex adsorbs the target gases, and the amount of gas adsorption per unit mass of this zeolite is larger than those of the metal-complex-including zeolites contrarily. The results probably relate to the fact that the metal-complex-including zeolite has a specific surface area smaller than that of the zeolite including no metal complex, because part of the pores of the zeolite is filled with the metal complex. Specifically, the gas adsorption behavior is reversed between the metal-complex-including zeolite and the zeolite including no metal complex at a certain concentration of the target gas.

As has been described above, it was verified that oscillation elements including a metal-complex-including zeolite supported on a quartz crystal resonator can highly sensitively detect target gases specifically at low concentrations (50 ppm or less) of the target gases. Such high-sensitivity detection of low concentration gases is not achieved by zeolite including no metal complex.

Next, the total absorption of the target gas was determined according to general Sauerbrey equation, i.e., following Equation (1):

(Equation 1)

$$\Delta F = -\frac{2F_0^2}{A\sqrt{\mu_q \rho_q}} \Delta m \quad (1)$$

In Equation (1), $\Delta F$ represents the amount of change in frequency; $F_0$ represents the fundamental resonance frequency of the quartz crystal resonator; "A" represents the electrode area; $\mu_q$ represents the shear stress of quartz; $\rho_q$ represents the density of quartz; and $\Delta m$ represents the amount of change in mass (amount of adsorbed gas). In the QCM chip used herein, $F_0$ is 10 MHz, "A" is 0.159 cm$^2$, $\mu_q$ is $2.947 \times 10^{10}$ kgm$^{-1}$s$^{-2}$, and $\rho_q$ is 2648 kgm$^{-3}$. Substitution of these values into Equation (1) gives following Equation (2):

(Equation 2)

$$\Delta m = -0.7 \Delta F \quad (2)$$

The change in frequency after one hour from the beginning of supply of the measurand gas was converted into an amount of change in mass (percent by weight) of each oscillation element sample according to Equation (2). Next, the number of moles (nmol) of adsorbed target gas molecules in each oscillation element sample was calculated from the above-converted value and the molecular weight of each target gas. The results are shown in Table 1.

TABLE 1

| VOC | NaX/QCM | | CoPc@NaX/QCM | |
|---|---|---|---|---|
| | wt. %[a] | nmol | wt. %[a] | nmol |
| Toluene | 0.054 | 0.14 | 0.402 | 1.76 |
| Pyridine | 0.216 | 0.29 | 1.643 | 2.77 |
| Acetaldehyde | 0.003 | 0.01 | 0.763 | 6.98 |

[a] Converted from change in frequency

As is shown in Table 1, the concrete values also demonstrate that CoPc@NaX/QCM and NaX/QCM are significantly different from each other in adsorption behavior with respect to each target gas at low concentrations of 20 ppm or less, concretely from 2 ppm to 12 ppm. Specifically, CoPc@NaX/QCM adsorbed each target gas in a number of moles about 10 times (10 to 700 times) that of NaX/QCM at the concentration of the target gas as tested herein.

In the oscillation element samples using CoPc@NaX/QCM, the numbers of moles of adsorbed molecules were converted into the numbers of adsorbed molecules per one molecule of CoPc. As a result, it was found that the sample E-1 supporting CoPc in an amount of $2.68 \times 10^{-9}$ adsorbed 0.57 molecule of toluene per one molecule of CoPc; the sample E-2 supporting CoPc in an amount of $0.89 \times 10^{-9}$ adsorbed 2.59 molecules of pyridine per one molecule of CoPc; and the sample E-3 supporting CoPc in an amount of $2.68 \times 10^{-9}$ adsorbed 2.70 molecules of acetaldehyde per one molecule of CoPc. As has been demonstrated above, the technique disclosed herein utilizes the fact that a metal-complex-including zeolite present on a quartz crystal resonator can effectively adsorb a target gas even in a low concentration (20 ppm or less, concretely from 2 ppm to 12 ppm), thereby allows the detection of the target gas with good sensitivity, and allows the determination of the amount of adsorbed target gas in molecular units.

While the above description is of the preferred embodiments of the present invention, it should be appreciated that the invention may be modified, altered, or varied without deviating from the scope and fair meaning of the following claims.

What is claimed is:

1. A method for detecting a low concentration gas contained in a measurand gas, the method comprising the steps of:
   supplying the measurand gas containing the target gas in a concentration of 50 ppm or less to an oscillation element, the oscillation element containing a quartz crystal resonator and a zeolite including a metal complex (hereinafter simply referred to as "metal-complex-including zeolite") present on or above the quartz crystal resonator, and
   detecting the target gas through a change in resonance frequency of the quartz crystal resonator, the change caused by the adsorption of the target gas by the metal-complex-including zeolite,
   wherein
   the zeolite is selected from the group consisting of zeolite X, zeolite Y, EMT, SAPO-37, and beryllophosphate X having an internal pore diameter of 1.3 nm and a pore opening diameter of 0.7 nm,
   the metal complex is a metal phthalocyanine complex encapsulated in a unit cell of the zeolite, and
   the metal-complex-including zeolite is just supported on an electrode of the quartz crystal resonator.

2. The method according to claim 1, wherein the oscillation element comprises a powder of the metal-complex-including zeolite supported on or above the quartz crystal resonator and contains substantially no binder.

3. The method according to claim 2, wherein the metal-complex-including zeolite is a zeolite X including a cobalt phthalocyanine complex encapsulated in a unit cell of the zeolite X.

4. A gas sensor for use in the method of claim 3, the gas sensor comprising:
   an oscillation element containing a quartz crystal resonator and a metal-complex-including zeolite present on or above the quartz crystal resonator;
   a measurand gas supply unit that supplies the measurand gas to the oscillation element; and,
   a frequency counter that determines the resonance frequency of the quartz crystal resonator.

5. A method for manufacturing an oscillation element for use in the method of claim 3, the manufacturing method comprising the steps of:
   preparing a powder of a zeolite including a metal complex, the metal complex having a size larger than that of the opening of a zeolite unit cell and being encapsulated in the zeolite unit cell;
   placing the powder of metal-complex-including zeolite in a solvent and homogenizing the powder in the solvent through ultrasonic disintegration to give a suspension containing substantially no binder; and,
   applying the suspension prepared through homogenization to a surface of an electrode of a quartz crystal resonator and drying the applied suspension.

6. A gas sensor for use in the method of claim 2, the gas sensor comprising:
   an oscillation element containing a quartz crystal resonator and a metal-complex-including zeolite present on or above the quartz crystal resonator;
   a measurand gas supply unit that supplies the measurand gas to the oscillation element; and,
   a frequency counter that determines the resonance frequency of the quartz crystal resonator.

7. A method for manufacturing an oscillation element for use in the method of claim 2, the manufacturing method comprising the steps of:
preparing a powder of a zeolite including a metal complex, the metal complex having a size larger than that of the opening of a zeolite unit cell and being encapsulated in the zeolite unit cell;
placing the powder of metal-complex-including zeolite in a solvent and homogenizing the powder in the solvent through ultrasonic disintegration to give a suspension containing substantially no binder; and,
applying the suspension prepared through homogenization to a surface of an electrode of a quartz crystal resonator and drying the applied suspension.

8. The method according to claim 1, wherein the metal-complex-including zeolite is a zeolite X including a cobalt phthalocyanine complex encapsulated in a unit cell of the zeolite X.

9. A gas sensor for use in the method of claim 8, the gas sensor comprising:
an oscillation element containing a quartz crystal resonator and a metal-complex-including zeolite present on or above the quartz crystal resonator;
a measurand gas supply unit that supplies the measurand gas to the oscillation element; and,
a frequency counter that determines the resonance frequency of the quartz crystal resonator.

10. A method for manufacturing an oscillation element for use in the method of claim 8, the manufacturing method comprising the steps of:
preparing a powder of a zeolite including a metal complex, the metal complex having a size larger than that of the opening of a zeolite unit cell and being encapsulated in the zeolite unit cell;
placing the powder of metal-complex-including zeolite in a solvent and homogenizing the powder in the solvent through ultrasonic disintegration to give a suspension containing substantially no binder; and,
applying the suspension prepared through homogenization to a surface of an electrode of a quartz crystal resonator and drying the applied suspension.

11. A gas sensor for use in the method of claim 1, the gas sensor comprising:
an oscillation element containing a quartz crystal resonator and a metal-complex-including zeolite present on or above the quartz crystal resonator;
a measurand gas supply unit that supplies the measurand gas to the oscillation element; and,
a frequency counter that determines the resonance frequency of the quartz crystal resonator.

12. A method for manufacturing an oscillation element for use in the method of claim 1, the manufacturing method comprising the steps of:
preparing a powder of a zeolite including a metal complex, the metal complex having a size larger than that of the opening of a zeolite unit cell and being encapsulated in the zeolite unit cell;
placing the powder of metal-complex-including zeolite in a solvent and homogenizing the powder in the solvent through ultrasonic disintegration to give a suspension containing substantially no binder; and,
applying the suspension prepared through homogenization to a surface of an electrode of a quartz crystal resonator and drying the applied suspension.

13. The method according to claim 1, wherein the target gas is selected from the group consisting of toluene, pyridine, acetaldehyde, and xylene.

14. The method according to claim 13, wherein the metal-complex-including zeolite is a zeolite X including a cobalt phthalocyanine complex encapsulated in a unit cell of the zeolite X.

15. A gas sensor for use in the method of claim 13, the gas sensor comprising:
an oscillation element containing a quartz crystal resonator and a metal-complex-including zeolite present on or above the quartz crystal resonator;
a measurand gas supply unit that supplies the measurand gas to the oscillation element; and,
a frequency counter that determines the resonance frequency of the quartz crystal resonator.

16. A method for manufacturing an oscillation element for use in the method of claim 13, the manufacturing method comprising the steps of:
preparing a powder of a zeolite including a metal complex, the metal complex having a size larger than that of the opening of a zeolite unit cell and being encapsulated in the zeolite unit cell;
placing the powder of metal-complex-including zeolite in a solvent and homogenizing the powder in the solvent through ultrasonic disintegration to give a suspension containing substantially no binder; and,
applying the suspension prepared through homogenization to a surface of an electrode of a quartz crystal resonator and drying the applied suspension.

* * * * *